(12) United States Patent
Schmid et al.

(10) Patent No.: US 11,981,757 B2
(45) Date of Patent: May 14, 2024

(54) INJECTION MOLDED MEDICAL DEVICES MADE FROM A HIGH MOLECULAR WEIGHT POLYETHYLENE

(71) Applicant: Celanese International Corporation, Irving, TX (US)

(72) Inventors: Christina Schmid, Darmstadt (DE); Rainer Walkenhorst, Melle (DE)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 0 days.

(21) Appl. No.: 16/826,475

(22) Filed: Mar. 23, 2020

(65) Prior Publication Data

US 2020/0308319 A1    Oct. 1, 2020

Related U.S. Application Data

(60) Provisional application No. 62/823,166, filed on Mar. 25, 2019.

(51) Int. Cl.
| | |
|---|---|
| *C08F 10/02* | (2006.01) |
| *A61K 47/32* | (2006.01) |
| *A61K 49/12* | (2006.01) |
| *A61K 49/22* | (2006.01) |
| *A61L 27/16* | (2006.01) |
| *A61L 29/04* | (2006.01) |
| *A61L 31/04* | (2006.01) |
| *B29C 45/00* | (2006.01) |
| *A61B 17/122* | (2006.01) |
| *A61B 90/98* | (2016.01) |
| *A61C 8/00* | (2006.01) |
| *A61F 5/00* | (2006.01) |
| *A61F 6/14* | (2006.01) |
| *A61J 15/00* | (2006.01) |
| *A61M 25/10* | (2013.01) |
| *A61N 1/36* | (2006.01) |
| *B29K 23/00* | (2006.01) |
| *B29K 105/00* | (2006.01) |
| *B29L 31/00* | (2006.01) |

(52) U.S. Cl.
CPC .............. *C08F 10/02* (2013.01); *A61K 47/32* (2013.01); *A61K 49/126* (2013.01); *A61K 49/22* (2013.01); *A61L 27/16* (2013.01); *A61L 29/041* (2013.01); *A61L 31/048* (2013.01); *B29C 45/0001* (2013.01); *A61B 17/122* (2013.01); *A61B 90/98* (2016.02); *A61C 8/0016* (2013.01); *A61F 5/005* (2013.01); *A61F 6/14* (2013.01); *A61J 15/00* (2013.01); *A61L 2430/02* (2013.01); *A61L 2430/06* (2013.01); *A61L 2430/20* (2013.01); *A61L 2430/22* (2013.01); *A61L 2430/24* (2013.01); *A61L 2430/30* (2013.01); *A61L 2430/38* (2013.01); *A61M 25/10* (2013.01); *A61N 1/36038* (2017.08); *A61N 1/3605* (2013.01); *B29K 2023/0675* (2013.01); *B29K 2105/0052* (2013.01); *B29L 2031/753* (2013.01); *B29L 2031/7532* (2013.01)

(58) Field of Classification Search
CPC ........ C08F 10/02; C08F 210/16; A61K 47/32; A61K 49/126; A61K 49/22; A61K 6/69; A61K 6/844; A61K 6/71; A61L 27/16; A61L 29/041; A61L 31/048; A61L 2430/02; A61L 2430/06; A61L 2430/20; A61L 2430/22; A61L 2430/24; A61L 2430/30; A61L 2430/38; A61L 27/50; A61L 27/54; A61L 29/14; A61L 29/16; A61L 29/18; A61L 31/14; A61L 31/16; A61L 31/18; B29C 45/0001; A61B 17/122; A61B 90/98; A61B 2017/00955; A61C 8/0016; A61F 5/005; A61F 6/14; A61J 15/00; A61M 25/10; A61N 1/36038; A61N 1/3605; B29K 2023/0675; B29K 2105/0052; B29L 2031/753; B29L 2031/7532

See application file for complete search history.

(56) References Cited

U.S. PATENT DOCUMENTS

| | | | |
|---|---|---|---|
| 3,775,521 | A | 11/1973 | Yamamoto et al. |
| 3,821,332 | A | 6/1974 | Solop |
| 4,164,531 | A | 8/1979 | Shiraki et al. |
| 5,422,061 | A | 6/1995 | Takahashi et al. |
| 6,414,086 | B1 | 7/2002 | Wang et al. |
| 6,818,171 | B2 | 11/2004 | Wang et al. |
| 6,849,224 | B2 | 2/2005 | Wang et al. |
| 9,745,462 | B2 | 8/2017 | Shen et al. |
| 9,822,224 | B2 | 11/2017 | Rufner et al. |

(Continued)

FOREIGN PATENT DOCUMENTS

| | | |
|---|---|---|
| WO | WO2011131322 A1 | 10/2011 |
| WO | WO2012004675 A2 | 1/2012 |

OTHER PUBLICATIONS

Ketchum, Career Trend 2018 (Year: 2018).*

(Continued)

*Primary Examiner* — Robert S Cabral
(74) *Attorney, Agent, or Firm* — DORITY & MANNING, P. A.

(57) ABSTRACT

A high molecular weight polyethylene polymer is formulated so that the polymer is capable of being injection molded. The polyethylene polymer has a Viscosity Number of greater than about 400 ml/g and has a melt flow rate of greater than about 0.9 g/10 min. The polyethylene polymer is of high purity and is particularly well suited for producing medical products.

20 Claims, No Drawings

(56) References Cited

U.S. PATENT DOCUMENTS

| | | |
|---|---|---|
| 2002/0040113 A1 | 4/2002 | Fritzsche et al. |
| 2003/0220451 A1 | 11/2003 | Wang et al. |
| 2004/0054054 A1 | 3/2004 | Blondel |
| 2005/0113935 A1 | 5/2005 | Wang et al. |
| 2007/0106002 A1 | 5/2007 | Tsujimoto |
| 2009/0105422 A1 | 4/2009 | Berthold et al. |
| 2010/0003439 A1 | 1/2010 | Michie, Jr. et al. |
| 2010/0261835 A1 | 10/2010 | Muller et al. |
| 2014/0051771 A1 | 2/2014 | Hufen et al. |
| 2017/0137303 A1 | 5/2017 | Hirsch et al. |

OTHER PUBLICATIONS

Griff, Film Lines (Canadian Plastics Industry Association, Winter 2003). (Year: 2013).*
European Search Report Corresponding to Application No. 20777538.8 on Nov. 18, 2022.
International Search Report Corresponding to Application No. PCT/US2020/024124 on Jun. 16, 2020.
'ISO 1628-3:2010 Plastics—Determination of the viscosity of polymers in dilute solution using capillary viscometers—Part 3: Polyethylenes and polypropylenes', iso.org, 2015.
Ticona, GUR ultra-high molecular weight polyethylene (PE-UHMW), 2001, 39 pages.
Translation of Japanese Office Action Corresponding to Application No. 2021-555619 on Dec. 15, 2023.

* cited by examiner

INJECTION MOLDED MEDICAL DEVICES MADE FROM A HIGH MOLECULAR WEIGHT POLYETHYLENE

RELATED APPLICATIONS

The present application is based upon and claims priority to U.S. Provisional Patent Application Ser. No. 62/823,166, having a filing date of Mar. 25, 2019, which is incorporated herein by reference.

BACKGROUND

Polyethylene has become established as an exceptionally useful engineering material in a variety of applications, in part because of its unique combination of desirable properties. For instance, high molecular weight polyethylene polymer particles may exhibit an improved abrasion resistance, chemical resistance, lubricity, impact strength, stress crack resistance, heat deflection temperature, wear resistance, and energy absorption capacity at high stress rates in comparison to other thermoplastic polymers.

High molecular weight polyethylene polymers generally include linear polyethylene polymers and can be differentiated from other polyethylene grades by a very high degree of polymerization. In fact, the high degree of polymerization is responsible for the fact that these polymers do not flow well when melted and, in fact, can display a melt flow index of 0 grams per 10 mins. Therefore, special processing methods like pressure sintering and ram extrusion are used to form these polymers into articles.

High molecular weight polyethylene polymers as described above, however, have various superior properties that make them desirable for a number of applications. For example, high molecular weight polyethylene polymers can have an extremely high impact strength, which is retained even at very low temperatures. In fact, high molecular weight polyethylene polymers can be produced that do not break when subjected to the notched impact strength test under ISO Test 179.

High molecular weight polyethylene polymers also have a relatively broad operating temperature range and are extremely wear resistant. In addition, high molecular weight polyethylene has great abrasion resistant properties which can be as good or better than steel.

High molecular weight polyethylene polymers can also be produced to be biocompatible. Thus, the polymers have been used in the past to produce various medical devices, such as orthopedic implants.

A need exists, however, for a high molecular weight polyethylene polymer that is capable of being injection molded for producing medical products. The ability to injection mold a high molecular weight polyethylene polymer, for instance, may allow the polymer to be used to produce smaller medical devices or to otherwise more efficiently produce various different types of medical products. Thus, a need exists for a high molecular weight polyethylene polymer capable of being injection molded that still retains many of the properties exhibited by low flow polyethylene polymers.

SUMMARY

The present disclosure is generally directed to a high molecular weight polyethylene polymer composition well suited for producing medical products. The high molecular weight polyethylene polymer, for instance, is biocompatible and can be used for all different types of medical applications, including implants, prosthetic devices, drug delivery devices, and the like. In accordance with the present disclosure, the high molecular weight polyethylene polymer is formulated so as to have melt flow properties sufficient for the polymer to be used in injection molding processes for producing the medical products.

In one embodiment, for instance, the present disclosure is directed to a medical device comprising an injection molded polymer article. The polymer article comprises a high molecular weight polyethylene polymer. The high molecular weight polyethylene polymer has a melt flow index of greater than about 0.8 g/10 min, such as greater than about 0.9 g/10 min and generally less than about 3 g/10 min, such as less than about 2 g/10 min when measured according to ISO Test 1133 at 190° C. and at a load of 21.6 kg. The high molecular weight polyethylene polymer can also have a Viscosity Number of greater than about 400 $cm^3/g$, such as greater than about 500 $cm^3/g$ and generally less than about 900 $cm^3/g$ when tested according to ISO Test 1628-3. The high molecular weight polyethylene polymer, for instance, can have a molecular weight of greater than about 350,000 g/mol, such as from about 500,000 g/mol to about 5,000,000 g/mol. As used herein, the molecular weight is determined according to ASTM Test D4020. The high molecular weight polyethylene polymer can have a specific gravity of from about 0.93 to about 0.97 $g/cm^3$ when tested according to ISO Test 1183-1, Method A.

The high molecular weight polyethylene polymer is biocompatible and can be produced to meet the test requirements of ISO Test 10993. For instance, the high molecular weight polyethylene polymer can pass ISO Test 10993-11 for systemic toxicity, can pass ISO Test 10993-10 for intracutaneous reactivity, can pass ISO Test 10993-6 for two weeks muscle implantation, can pass ISO Test 10993-5 for cytotoxicity, can pass ISO Test 10993-3 for genotoxicity, can pass ISO Test 10993-4 for hemolysis, and can pass USP Test 661 for physicochemical.

The polymer article of the present disclosure can be made primarily from the high molecular weight polyethylene polymer. For instance, the polymer article can contain the high molecular weight polyethylene polymer in an amount greater than about 70% by weight, such as in an amount greater than about 80% by weight, such as in an amount greater than about 90% by weight, such as in an amount greater than about 95% by weight. The high molecular weight polyethylene polymer can be a homopolymer or can comprise a copolymer. For instance, in one embodiment, the high molecular weight polyethylene polymer can be a copolymer of ethylene and at least one monomer comprising propylene, butylene, or mixtures thereof. In one embodiment, the high molecular weight polyethylene polymer can be used to produce articles and then crosslinked.

The polymer article can contain various other ingredients in addition to the high molecular weight polyethylene polymer. For instance, the polymer article may contain an active pharmaceutical ingredient, an imaging agent, a reinforcing material, and the like.

All different types of medical devices can be made from the high molecular weight polyethylene polymer. For instance, the medical device may comprise a prosthetic or an implant. In one embodiment, the medical device may have a tubular shape for conveying liquids or for coating an electrical element, such as a wire.

In one embodiment, the polymer article can be incorporated into a chip, an RFID device, a pump, a surgical instrument, or a neurostimulator. In other embodiments, the polymer article may comprise a feeding tube, a catheter, an inflatable balloon, a stint, a heart valve, a cochlear implant, a cranio-maxillofacial implant, synthetic cartilage, a stomach ring, a blood vessel clamp, an aneurysm clip, a spinal plug, a base-plate stem cap for an artificial joint, a muscle implant, a nasopharyngeal implant, a laryngeal implant, an oromucosal insert, an intrauterine device, an intravaginal ring, or a dental fiber. In still another embodiment, the medical device may comprise a drug delivery device, a transdermal patch, or a subdermal implant.

The present disclosure is also directed to a method for injection molding a medical product. In still another embodiment, the present disclosure is directed to a method for implanting the medical devices described above into a patient.

Other features and aspects of the present disclosure are discussed in greater detail below.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a polyethylene composition comprising a high molecular weight polyethylene polymer that is not only biocompatible but is also capable of being melt processed through injection molding. The polyethylene polymer composition is well suited for producing all different types of medical products. Because the polymer composition can be injection molded, the polyethylene polymer composition is particularly well suited to producing small medical devices or other medical articles where injection molding provides advantages with respect to production efficiency or provides various other benefits and advantages.

The polyethylene polymer present in the polymer composition has a molecular weight as high as possible while still being capable of being injection moldable. The polyethylene polymer, for instance, is a high molecular weight polyethylene polymer that has a melt flow rate of at least about 0.5 g/10 min, such as at least about 0.7 g/10 min, such as at least about 0.9 g/10 min, such as at least about 1.1 g/10 min, such as at least about 1.3 g/10 min and generally less than about 2.5 g/10 min, such as less than about 2.3 g/10 min, such as less than about 2 g/10 min, such as less than about 1.8 g/10 min. Melt flow index is measured according to ISO Test 1133 at a temperature of 190° C. and at a load of 21.6 kg.

The high molecular weight polyethylene polymer is of high purity and is biocompatible. More particularly, the polyethylene polymer in the composition of the present disclosure passes at least most of the requirements of ISO Test 10993. For example, the polyethylene polymer passes ISO Test 10993-11 for systemic toxicity, passes ISO Test 10993-10 for intracutaneous reactivity, passes ISO Test 10993-6 for two weeks muscle implantation, passes ISO Test 10993-5 for cytotoxicity, passes ISO Test 10993-3 for genotoxicity, passes ISO Test 10993-4 for hemolysis, and passes USP Test 661 for physicochemical.

The high molecular weight polyethylene may be a homopolymer, a copolymer, or a blend thereof. In one embodiment, the polyethylene may be a homopolymer.

In another embodiment, the polyethylene may be a copolymer. For instance, the polyethylene may be a copolymer of ethylene and another olefin containing from 3 to 16 carbon atoms, such as from 3 to 10 carbon atoms, such as from 3 to 8 carbon atoms. These other olefins include, but are not limited to, propylene, 1-butene, 1-pentene, 1-hexene, 1-heptene, 1-octene, 4-methylpent-1-ene, 1-decene, 1-dodecene, 1-hexadecene and the like. Also utilizable herein are polyene comonomers such as 1,3-hexadiene, 1,4-hexadiene, cyclopentadiene, dicyclopentadiene, 4-vinylcyclohex-1-ene, 1,5-cyclooctadiene, 5-vinylidene-2-norbornene and 5-vinyl-2-norbornene. However, when present, the amount of the non-ethylene monomer(s) in the copolymer may be less than about 10 mol. %, such as less than about 5 mol. %, such as less than about 2.5 mol. %, such as less than about 1 mol. %, wherein the mol. % is based on the total moles of monomer in the polymer.

In one embodiment, the polyethylene may exhibit a bimodal molecular weight distribution. For instance, a bimodal distribution generally refers to a polymer having a distinct higher molecular weight and a distinct lower molecular weight (e.g. two distinct peaks) on a gel permeation chromatography curve. In another embodiment, the polyethylene may exhibit more than two molecular weight distribution peaks such that the polyethylene exhibits a multimodal (e.g., trimodal, tetramodal, etc.) distribution. Alternatively, the polyethylene may exhibit a broad molecular weight distribution wherein the polyethylene is comprised of a blend of higher and lower molecular weight components such that the size exclusion chromatography or gel permeation chromatography curve does not exhibit at least two distinct peaks but instead exhibits one distinct peak broader than the individual component peaks.

In one embodiment, the composition may be comprised of more than one polyethylene polymer, each having a different molecular weight and/or molecular weight distribution. For instance, the molecular weight distribution may be within the average molecular weight specifications provided above.

In addition, the composition may be comprised of a blend of one or more polyethylene polymers or copolymers and another thermoplastic polymer such as a polypropylene or a polybutylene. However, the amount of non-polyethylene polymer(s) in the composition may be less than about 10 wt. %, such as less than about 5 wt. %, such as less than about 2.5 wt. %, such as less than about 1 wt. %, wherein the wt % is based on the total weight of the composition.

Any method known in the art can be utilized to synthesize the polyethylene. The high molecular weight polyethylene powder is typically produced by the catalytic polymerization of ethylene monomer or optionally with one or more other 1-olefin co-monomers, the 1-olefin content in the final polymer being less or equal to 10% of the ethylene content, with a heterogeneous catalyst and an organo aluminum or magnesium compound as cocatalyst. The ethylene is usually polymerized in gaseous phase or slurry phase at relatively low temperatures and pressures. The polymerization reaction may be carried out at a temperature of between 50° C. and 100° C. and pressures in the range of 0.02 and 2 MPa.

The molecular weight of the polyethylene can be adjusted by adding hydrogen. Altering the temperature and/or the type and concentration of the co-catalyst may also be used to fine tune the molecular weight. Additionally, the reaction may occur in the presence of antistatic agents to avoid wall fouling and product contamination.

Suitable catalyst systems include but are not limited to Ziegler-Natta type catalysts. Typically Ziegler-Natta type catalysts are derived by a combination of transition metal compounds of Groups 4 to 8 of the Periodic Table and alkyl or hydride derivatives of metals from Groups 1 to 3 of the Periodic Table. Transition metal derivatives used usually comprise the metal halides or esters or combinations thereof.

Exemplary Ziegler-Natta catalysts include those based on the reaction products of organo aluminum or magnesium compounds, such as for example but not limited to aluminum or magnesium alkyls and titanium, vanadium or chromium halides or esters. The heterogeneous catalyst might be either unsupported or supported on porous fine grained materials, such as silica or magnesium chloride. Such support can be added during synthesis of the catalyst or may be obtained as a chemical reaction product of the catalyst synthesis itself.

In one embodiment, a suitable catalyst system can be obtained by the reaction of a titanium(IV) compound with a trialkyl aluminum compound in an inert organic solvent at temperatures in the range of −40° C. to 100° C., preferably −20° C. to 50° C. The concentrations of the starting materials are in the range of 0.1 to 9 mol/L, preferably 0.2 to 5 mol/L, for the titanium(IV) compound and in the range of 0.01 to 1 mol/L, preferably 0.02 to 0.2 mol/L for the trialkyl aluminum compound. The titanium component is added to the aluminum component over a period of 0.1 min to 60 min, preferably 1 min to 30 min, the molar ratio of titanium and aluminum in the final mixture being in the range of 1:0.01 to 1:4.

In another embodiment, a suitable catalyst system is obtained by a one or two-step reaction of a titanium(IV) compound with a trialkyl aluminum compound in an inert organic solvent at temperatures in the range of −40° C. to 200° C., preferably −20° C. to 150° C. In the first step the titanium(IV) compound is reacted with the trialkyl aluminum compound at temperatures in the range of −40° C. to 100° C., preferably −20° C. to 50° C. using a molar ratio of titanium to aluminum in the range of 1:0.1 to 1:0.8. The concentrations of the starting materials are in the range of 0.1 to 9.1 mol/L, preferably 5 to 9.1 mol/L, for the titanium (IV) compound and in the range of 0.05 and 1 mol/L, preferably 0.1 to 0.9 mol/L for the trialkyl aluminum compound. The titanium component is added to the aluminum compound over a period of 0.1 min to 800 min, preferably 30 min to 600 min. In a second step, if applied, the reaction product obtained in the first step is treated with a trialkyl aluminum compound at temperatures in the range of −10° C. to 150° C., preferably 10° C. to 130° C. using a molar ratio of titanium to aluminum in the range of 1:0.01 to 1:5.

In yet another embodiment, a suitable catalyst system is obtained by a procedure wherein, in a first reaction stage, a magnesium alcoholate is reacted with a titanium chloride in an inert hydrocarbon at a temperature of 50° to 100° C. In a second reaction stage the reaction mixture formed is subjected to heat treatment for a period of about 10 to 100 hours at a temperature of 110° to 200° C. accompanied by evolution of alkyl chloride until no further alkyl chloride is evolved, and the solid is then freed from soluble reaction products by washing several times with a hydrocarbon.

In a further embodiment, catalysts supported on silica, such as for example the commercially available catalyst system Sylopol 5917 can also be used.

Using such catalyst systems, the polymerization is normally carried out in suspension at low pressure and temperature in one or multiple steps, continuous or batch. The polymerization temperature is typically in the range of 30° C. to 130° C., preferably is the range of 50° C. and 90° C. and the ethylene partial pressure is typically less than 10 MPa, preferably 0.05 and 5 MPa. Trialkyl aluminums, like for example but not limited to isoprenyl aluminum and triisobutyl aluminum, are used as co-catalyst such that the ratio of Al:Ti (co-catalyst versus catalyst) is in the range of 0.01 to 100:1, more preferably is the range of 0.03 to 50:1.

The solvent is an inert organic solvent as typically used for Ziegler type polymerizations. Examples are butane, pentane, hexane, cyclohexene, octane, nonane, decane, their isomers and mixtures thereof. The polymer molecular mass is controlled through feeding hydrogen. The ratio of hydrogen partial pressure to ethylene partial pressure is in the range of 0 to 50, preferably the range of 0 to 10. The polymer is isolated and dried in a fluidized bed drier under nitrogen. The solvent may be removed through steam distillation in case of using high boiling solvents. Salts of long chain fatty acids may be added as a stabilizer. Typical examples are calcium, magnesium and zinc stearate.

Optionally, other catalysts such as Phillips catalysts, metallocenes and post metallocenes may be employed. Generally a cocatalyst such as alumoxane or alkyl aluminum or alkyl magnesium compound is also employed. For example, U.S. Patent Application Publication No. 2002/0040113 to Fritzsche et al., the entire contents of which are incorporated herein by reference, discusses several catalyst systems for producing high molecular weight polyethylene. Other suitable catalyst systems include Group 4 metal complexes of phenolate ether ligands such as are described in International Patent Publication No. WO2012/004675, the entire contents of which are incorporated herein by reference.

As used herein, a polyethylene may have an average molecular weight, as determined according to ASTM Test D4020, of at least or greater than 100,000 g/mol, such as at least about 200,000 g/mol, such as at least about 300,000 g/mol, such as at least about 350,000 g/mol, such as at least about 450,000 g/mol, such as at least about 500,000 g/mol, such as at least about 600,000 g/mol, such as greater than about 1,000,000 g/mol, such as greater than about 1,500,000 g/mol, such as greater than about 2,000,000 and generally less than about 5,000,000 g/mol, such as less than about 3,000,000 g/mol, such as less than about 1,000,000 g/mol. For example, the average molecular weight of the polymer can be greater than about 300,000 g/mol and less than about 5,000,000 g/mol including all increments of 25,000 g/mol therebetween.

The polyethylene may be manufactured in the form of a powder such as a micropowder. For instance, the polyethylene power may be a free-flowing powder. The polyethylene powder can have a multi-lobal (popcorn-like) morphology. The powder may have an average particle size, d50, of no more than 2,000 μm, such as between about 10 and about 1,500 μm, such as from about 50 μm to about 650 μm, such as from about 50 to about 400 μm, such as from about 50 to about 200 μm. Preferably, the as-synthesized polymer has the desired particle size. However, if the as-synthesized polymer has a particle size in excess of the desired value, the particles can be ground to the desired particle size. The powder particle size can be measured utilizing a laser diffraction method according to ISO 13320.

The polyethylene may have a viscosity number of at least 100 mL/g, such as at least 200 mL/g, such as at least 300 mL/g, such as at least 400 mL/g, such as at least 500 mL/g to less than about 2,000 mL/g, such as less than about 1,500 mL/g, such as less than about 1,000 mL/g, such as less than about 800 mL/g, such as less than about 600 mL/g, as determined according to ISO 1628 part 3 utilizing a concentration in decahydronapthalene of 0.0002 g/mL.

The polyethylene may be present in the composition in an amount of greater than about 70 wt. %, such as greater than about 75 wt. %, such as greater than about 80 wt. %, such as greater than about 85 wt. %, such as greater than about 90 wt. %, such as greater than about 95 wt. %, such as greater than about 98 wt. % and less than about 100 wt. %, such as less than about 98 wt. %, such as less than about 95 wt. %. The above amounts can refer to a single high molecular weight polyethylene polymer or may refer to a blend of high molecular weight polyethylene polymers. In one embodiment, however, only a single high molecular weight polyethylene polymer is used to produce the polymer articles.

As described above, the high molecular weight polyethylene polymer is generally of high purity. In this regard, the high molecular weight polyethylene polymer can have an ash content of less than about 500 ppm, such as less than about 250 ppm, such as less than about 100 ppm, such as less than about 50 ppm, such as less than about 10 ppm. The high molecular weight polyethylene polymer can generally have a specific gravity when tested according to ISO Test 1183 of generally greater than about 0.93 g/cm$^3$, such as greater than about 0.94 g/cm$^3$, such as greater than about 0.95 g/cm$^3$, and generally less than about 0.97 g/cm$^3$.

The polymer composition and polymer article produced therefrom may also contain other known additives such as, for example, antioxidants, UV stabilizers, light stabilizers, heat stabilizers, reinforcing fibers or fillers, lubricants, optical brighteners, colorants, demolding agents, crosslinking agents, plasticizers, pigments, antistatic agents, and the like. In one embodiment, any polymer additive present in the polymer article is biocompatible.

Antioxidants may, in some embodiments, mitigate oxidation and/or chemical degradation of polyethylene compositions described herein during storage, transportation, and/or implementation (in vivo and/or ex vivo). Examples of antioxidants suitable for use in conjunction with the polyethylene compositions described herein may, in some embodiments, include, but are not limited to, ascorbic acid, glutathione, lipoic acid, uric acid, resveratrol, flavonoids, carotenes (e.g., beta-carotene), carotenoids, tocopherols (e.g., alpha-tocopherol), tocotrienols, ubiquinol, melatonin, secondary aromatic amines, benzofuranones, hindered phenols, polyphenols, hindered amines, organophosphorus compounds, thioesters, benzoates, lactones, hydroxylamines, and any combination thereof.

Reinforcing fillers may, in some embodiments, inter alia, enhance the mechanical strength of polyethylene compositions described herein. Examples of reinforcing fillers suitable for use in conjunction with the polyethylene compositions described herein may, in some embodiments, include, but are not limited to, glass spheres, glass fibers, bioglass, graphite, aluminum powder, talc, chalk, silicates, carbonates, calcium carbonate, alumina trihydrate, marble dust, cement dust, clay, feldspar, fumed silica, alumina, magnesium oxide, magnesium hydroxide, antimony oxide, zinc oxide, barium sulfate, aluminum silicate, calcium silicate, titanium dioxide, titanates, glass microspheres, carbon fibers, metallic fibers, carbon nanotubes, wood flour, carbon black, and the like, and any combination thereof.

Examples of pigments and/or dyes suitable for use in conjunction with polyethylene compositions described herein may, in some embodiments, include, but are not limited to, inorganic-based colorants, organic-based colorants, and the like, and any combination thereof.

Examples of antifouling agents suitable for use in conjunction with polyethylene compositions described herein may, in some embodiments, include, but are not limited to, sulfoamides, penicillin, cephalosorins, carbapenems, quinolones, oxazolidones, quaternary ammonium compounds, nobel metals (e.g., silver, gold, copper, and the like), amine containing polymers, and the like, and any combination thereof.

These additives may be used singly or in any combination thereof. In general, unless stated otherwise, if the additives are utilized, they may be present in an amount of at least about 0.05 wt. %, such as at last about 0.1 wt. %, such as at least about 0.25 wt. %, such as at least about 0.5 wt. %, such as at least about 1 wt. % and generally less than about 20 wt. %, such as less than about 10 wt. %, such as less than about 5 wt. %, such as less than about 4 wt. %, such as less than about 2 wt. %. The sum of the wt. % of all of the components, including any additives if present, utilized in the polymer composition will be 100 wt. %.

In one embodiment, the polyethylene polymer composition can contain an active pharmaceutical ingredient and/or at least one imaging agent. The active pharmaceutical ingredient can be surface coated onto the polymer article or can be homogeneously mixed with the polymer. In general, any suitable active pharmaceutical ingredient can be incorporated into the polymer article.

An imaging agent can also be incorporated into the polymer article that interacts with electromagnetic radiation so that the polymer article can be better identified through x-rays or other imaging systems. Examples of imaging agents suitable for use in conjunction with the polyethylene compositions described herein may, in some embodiments, include, but are not limited to, magnetic resonance imaging agents (e.g., barium sulfate, iron oxide particles, gadolinium compounds, erbium compounds, gadolinium endofullerenes, and gadolinium endonanotubes), x-ray imaging agents (e.g., barium sulfate, iodine compounds, and iodine endonanotubes), ultrasound imaging agents (e.g., perfluorocarbons and air bubbles), near infrared imaging agents (e.g., carbon nanotubes, gold nanoparticles, silver nanoparticles, and gold nanoshells), bismuth compounds, tungsten compounds, and the like, and any combination thereof. In general, an imaging agent can be present in the polymer composition in an amount from about 0.01% by weight to about 5% by weight.

The polymer composition of the present disclosure can be used to produce numerous different types of medical products. For instance, the polyethylene polymer composition can be used to produce prosthetic devices, implants, and the like. The polymer composition can also be used to produce medical instruments, and all different types of tubular devices such as catheters, inhalers, and the like.

Examples of medical products that may be made in accordance with the present disclosure include, but are not limited to, chips, RFID tags, tubing, pumps, feeding tubes, catheters, vascular catheters, prosthesis, inflatable balloons, stents, heart valves, neurostimulators, cochlear implants, cranio-maxillofacial implants, synthetic cartilage, stomach rings, surgical instruments, blood vessel clamps, aneurysm clamps, spinal plugs for use in conjunction with a joint fusion system, base plates for use in artificial joints, muscle implants, nasopharyngeal implants, laryngeal implants, drug delivery devices, transdermal patches, subdermal implants, oromucosal inserts, intrauterine devices, intravaginal rings, dental fibers, hip implants, tibia implants, a wrist implant, hand implants, parts thereof, and the like.

In some embodiments, molded polyethylene components of the present invention may be a conduit that comprises at least one wall defining an internal volume, the at least one wall comprising polyethylene compositions described herein.

In some embodiments, a conduit molded polyethylene component may be designed to allow fluid to flow through the internal volume. For example, biomedical devices like pumps, tubings, feeding tubes, catheters, vascular catheters, stents, heart valves, surgical instruments (e.g., surgical suction instruments), nasopharyngeal implants, and laryngeal implants may each comprise at least one conduit molded polyethylene component designed to allow fluid to flow through the internal volume.

In some embodiments, a conduit molded polyethylene component may have at least one wire disposed within the internal volume. By way of nonlimiting example, in some embodiments, a biomedical device (e.g., a pacemaker) may comprise at least one wire having a conduit molded polyethylene component disposed thereabout.

In some embodiments, molded polyethylene components described herein may be the primary composition of a biomedical device (e.g., cranio-maxillofacial implants). In some instances, the polyethylene compositions of the molded polyethylene components may comprise polyethylene and a bioabsorbable polymer, such that when implemented, the bioabsorbable polymer is absorbed leaving voids in the polyethylene composition.

In some embodiments, molded polyethylene components of the present invention may substantially encase other components of a biomedical device. In some embodiments, the encasement may be such that when implanted in a patient the surrounding tissue may be primarily exposed to the molded polyethylene component. In some embodiments, encasement may be achieved by over molding, thermoforming, or shrink wrapping a polyethylene composition described herein at least partially about the other components to be encased. In some embodiments, encasement may be achieved by forming a molded polyethylene component appropriately sized for placement of a biomedical device and/or component thereof therein.

By way of nonlimiting example, in some embodiments, a biomedical device, e.g., a cochlear implant or an RFID tag, may be substantially encased in a molded polyethylene component, such that the molded polyethylene component resembles a coating disposed substantially about the biomedical device. By way of another nonlimiting example, a biomedical device, e.g., a pacemaker or a neurostimulator, may comprise a molded polyethylene component that comprises a wire having a coating disposed substantially thereabout, the coating comprising a polyethylene composition described herein. By way of another nonlimiting example, the power supply for a neurostimulator may comprise a molded polyethylene component substantially encasing the power supply, e.g., achieved by over molding, thermoforming, or shrink wrapping.

In some embodiments, molded polyethylene components described herein may be a drug delivery device or portion thereof. In some embodiments, a transdermal patch may comprise a backing, a medicated layer, and a release layer, wherein the molded polyethylene component may be the medicated layer and/or the release layer. By way of nonlimiting example, the medicated layer may be a molded polyethylene component and the release layer may comprise a second polymer (e.g., an ethylene copolymer like ethylene vinyl acetate). In some instances, the molded polyethylene component may comprise polyethylene and a second polymer. In some instances, the medicated layer and the release layer may independently be molded polyethylene components with different compositions.

Similar to the transdermal patch examples, other drug delivery devices may comprise molded polyethylene components. For example, a vaginal ring with a core similar to the medicated layer above and the sheath similar to the release layer above. In another example, a subdermal implant like a rod or sheet with a multi-layer structure may have at least one layer similar to the medicated layer and at least one layer similar to the release layer described above.

The high molecular weight polyethylene polymer composition of the present disclosure can be formed into medical products using various different techniques. However, the polymer composition is particularly well suited to injection molding.

During melt forming, the polymer composition can generally be heated to a temperature of greater than about 100° C. to about 300° C. In one embodiment, the polymer composition can be crosslinked after the polymer article is formed. In one embodiment, for instance, the polymer composition may contain a crosslinking agent in an amount from about 0.001% by weight to about 1% by weight. Crosslinking agents that may be used include, for instance, peroxides or silanes. The polymer can be crosslinked using electron beam crosslinking or gamma irradiation.

The following example demonstrates injection molding a polymer composition in accordance with the present disclosure.

EXAMPLE

A high molecular weight polyethylene polymer is formulated in accordance with the present disclosure. The high molecular weight polyethylene polymer had a melt flow rate of 1.1 g/10 min when tested at 190° C. and at a load of 21.6 kg. The polyethylene polymer had a Viscosity Number of 500 ml/g.

To demonstrate that the high molecular weight polymer was capable of being injection molded, the polymer was formed into an ISO tensile bar using injection molding.

During injection molding, the total shot weight was 25 grams. The injection molding device was run such that Zone 1 was at 52° C., Zone 2 was at 188° C., Zone 3 was at 238° C., Zone 4 was at 274° C., and the nozzle was at 260° C. The mold temperature was 70° C. The injection velocity was 25 mm/s and the injection pressure was 686 bar.

During injection molding, the hold time was 12 seconds, the cool time was 35 seconds, and the screw recovery time was 15.7 seconds. The cycle time was 63 seconds, the screw rotation speed was 225 rpm and the back pressure was 69 bar.

The ISO tensile bar was successfully injection molded. The tensile bar was tested for elongational stress according to ISO Test 11542-2. The tensile bar had an elongational stress of less than 0.05 MPa.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A medical device comprising:
    an injection molded polymer article, the polymer article comprising a high molecular weight polyethylene polymer, the high molecular weight polyethylene polymer contained in the polymer article having a melt flow index of greater than about 0.8 g/10 min and less than 2.5 g/10 min as measured by ISO Test 1133 at 190° C. and at a load of 21.6 kg, the high molecular weight polyethylene contained in the polymer article having a Viscosity Number of greater than about 400 cm$^3$/g and less than about 900 cm$^3$/g when tested according to ISO Test 1628-3, and wherein the high molecular weight polyethylene polymer contained in the polymer article is also a high density polyethylene polymer having a specific gravity of from about 0.94 g/cm$^3$ to about 0.97 g/cm$^3$ when tested according to ISO Test 1183-1, Method A, and wherein the injection molded article contains the high molecular weight polyethylene polymer in an amount greater than about 80% by weight.

2. A medical device as defined in claim 1, wherein the high molecular weight polyethylene polymer has a melt flow index of from about 0.9 g/10 min to about 2.0 g/10 min.

3. A medical device as defined in claim 1, wherein the high molecular weight polyethylene polymer has a Viscosity Number of greater than about 450 cm$^3$/g and less than about 900 cm$^3$/g.

4. A medical device as defined in claim 1, wherein the high molecular weight polyethylene polymer has a molecular weight of greater than about 300,000 g/mol and less than about 5,000,000 g/mol according to ASTM Test D4020.

5. A medical device as defined in claim 4, wherein the high molecular weight polyethylene polymer has a molecular weight of from about 350,000 g/mol to about 5,000,000 g/mol according to ASTM Test D4020.

6. A medical device as defined in claim 1, wherein the high molecular weight polyethylene polymer has a specific gravity of from about 0.95 g/cm$^3$ to about 0.97 g/cm$^3$ when tested according to ISO Test 1183-1, Method A.

7. A medical device as defined in claim 1, wherein the high molecular weight polyethylene polymer meets the test requirements of ISO Test 10993.

8. A medical device as defined in claim 7, wherein the high molecular weight polyethylene polymer passes ISO Test 10993-11 for systemic toxicity, passes ISO Test 10993-10 for intracutaneous reactivity, passes ISO Test 10993-6 for two weeks muscle implantation, passes ISO Test 10993-5 for cytotoxicity, passes ISO Test 10993-3 for genotoxicity, passes ISO Test 10993-4 for hemolysis, and passes USP Test 661 for physicochemical.

9. A medical device as defined in claim 1, wherein the injection molded polymer article contains the high molecular weight polyethylene polymer in an amount greater than about 90% by weight.

10. A medical device as defined in claim 1, wherein the high molecular weight polyethylene polymer comprises a copolymer of ethylene and at least one monomer comprising propylene, butylene, or mixtures thereof.

11. A medical device as defined in claim 1, wherein the molded polymer article further contains an active pharmaceutical ingredient.

12. A medical device as defined in claim 1, wherein the polymer article further contains an imaging agent.

13. A medical device as defined in claim 1, wherein the polymer article comprises a prosthetic device.

14. A medical device as defined in claim 1, wherein the polymer article comprises an implant.

15. A medical device as defined in claim 1, wherein the polymer article has a tubular shape.

16. A medical device as defined in claim 1, wherein the polymer article is incorporated into a chip, an RFID tag, a surgical instrument, a neurostimulator, or a pump.

17. A medical device as defined in claim 1, wherein the polymer article comprises a feeding tube, a catheter, an inflatable balloon, a stint, a heart valve, a cochlear implant, a cranio-maxillofacial implant, synthetic cartilage, a stomach ring, a blood vessel clamp, an aneurysm clip, a spinal plug, a base-plate stem cap for an artificial joint, a muscle implant, a nasopharyngeal implant, a laryngeal implant, an oromucosal insert, an intrauterine device, an intravaginal ring, or a dental fiber.

18. A medical device as defined in claim 1, wherein the polymer article comprises a drug delivery device, a transdermal patch, or a subdermal implant.

19. A method comprising:
implanting the medical device as defined in claim 1 into a patient.

20. A medical device as defined in claim 10, wherein the high molecular weight polyethylene polymer is a copolymer of ethylene and at least one monomer comprising propylene, butylene, or mixtures thereof.

* * * * *